United States Patent
Magne-Drisch et al.

(10) Patent No.: US 6,528,695 B1
(45) Date of Patent: *Mar. 4, 2003

(54) PROCESS FOR THE PRODUCTION OF AN ISOMER OF XYLENES IN THREE STAGES: SEPARATION, ISOMERIZATION IN THE PRESENCE OF A CATALYST BASED ON AN EUO ZEOLITE AND TRANSALKYLATION

(75) Inventors: Julia Magne-Drisch, Vilette de Vienne (FR); Gérard Hotier, Chaponost (FR); Jean-François Joly, Lyons (FR); Elisabeth Merlen, Rueil-Malmaison (FR); Fabio Alario, Neuilly sur Seine (FR)

(73) Assignee: Institut Francais du Petrole, Rueil Malmaison Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/598,486

(22) Filed: Jun. 22, 2000

(30) Foreign Application Priority Data

Jun. 22, 1999 (FR) .............................................. 9907967

(51) Int. Cl.$^7$ ........................... C07C 15/12; C07C 5/22; C07C 5/52

(52) U.S. Cl. ....................... 585/477; 585/478; 585/475; 585/470; 585/479

(58) Field of Search ................................ 585/477, 478, 585/479, 470, 475

(56) References Cited

U.S. PATENT DOCUMENTS

| 3,716,597 | A | * | 2/1973 | Mitsche et al. | ............. 260/671 |
| 4,021,499 | A | * | 5/1977 | Bieser | ......................... 260/674 |
| 4,341,914 | A | | 7/1982 | Berger | |
| 4,537,754 | A | | 8/1985 | Casci et al. | |
| 4,783,568 | A | | 11/1988 | Schmidt | ...................... 585/477 |
| 5,284,992 | A | | 2/1994 | Hotier et al. | |

FOREIGN PATENT DOCUMENTS

| EP | 0 051 318 | | 5/1982 |
| EP | 0 923 987 A1 | | 6/1999 |
| EP | 0 923 987 | | 6/1999 |
| FR | 2 768 724 | | 3/1999 |
| JP | 50-16780 | | 6/1975 |
| JP | 355164631 | * | 12/1980 |

* cited by examiner

Primary Examiner—Walter D. Griffin
Assistant Examiner—Tam M. Nguyen
(74) Attorney, Agent, or Firm—Millen, White, Zelano & Branigan, P.C.

(57) ABSTRACT

The invention relates to a process for the production of at least one isomer of xylenes, preferably paraxylene, as well as benzene, starting from a C8-aromatic fraction, whereby said process comprises a zone for separation of xylenes, a zone for isomerization of aromatic compounds with 8 carbon atoms used in the presence of a catalyst that comprises at least one EUO-structural-type zeolite that is selected from among the EU-1, TPZ-3, ZSM-50 zeolites and at least one metal of group VIII of the periodic table, and finally a transalkylation zone of C7- and C9-aromatic compounds. The invention makes it possible to produce paraxylene and benzene with a high yield, starting from a C8-aromatic fraction that comprises a large amount of ethylbenzene with improved performance levels of the isomerization stage and a good conversion of ethylbenzene in the transalkylation stage.

28 Claims, 1 Drawing Sheet

PROCESS FOR THE PRODUCTION OF AN ISOMER OF XYLENES IN THREE STAGES: SEPARATION, ISOMERIZATION IN THE PRESENCE OF A CATALYST BASED ON AN EUO ZEOLITE AND TRANSALKYLATION

FIELD OF THE INVENTION

The invention relates to a process for the production of benzene and at least one isomer of xylenes that is selected from among metaxylene, paraxylene and orthoxylene, starting from a feedstock that comprises aromatic hydrocarbons with 8 carbon atoms per molecule. The process applies particularly to the synthesis of very pure paraxylene for producing an intermediate petrochemical product, terephthalic acid. The process also applies to the synthesis of benzene that is used in particular for producing phenylalkanes by alkylation of benzene with mono-olefins, whereby the phenylalkanes constitute compounds for the formulation, after sulfonation, of biodegradable detergents.

PRIOR ART

The production of the specific isomer of xylenes is a significant petrochemical process in the synthesis of polyesters, used in particular in the fabric manufacturing industry. It then is important to be able to produce the desired isomer, preferably paraxylene, with maximum purity. Several techniques for separating isomers have been developed. Thus, the separation of the isomers can be done by adsorption, for example in a zeolitic sieve, which delivers a fraction that is very high in paraxylene and a fraction that is low in paraxylene and therefore high in orthoxylene and metaxylene, in the presence of an elution solvent. Since the composition of the aromatic feedstocks with 8 carbon atoms varies broadly according to their origin, however, whereby the content of para and ortho isomer generally approaches 50% relative to the total amount of xylenes, a single process does not make it possible to maximize the production of the desired xylene isomer. It is then necessary to combine an adsorption stage of the feedstock followed by an isomerization stage of this fraction that is low in the desired isomer as is described in Patent GB 1 420 796. Patent EP 531 191 of the applicant describes a process for the production of paraxylene by treatment in an adsorption zone followed by a crystallization stage of the adsorbed paraxylene, whereby the raffinate that is low in paraxylene is sent into an isomerization zone.

During this isomerization stage, the ratio of isomers at equilibrium is reestablished since the desired isomers are produced at the expense of the remaining isomers. The catalyst that is used in the isomerization reactions can be mordenite mixed with other zeolites such as the ZSM-5 zeolite as described in U.S. Pat. Nos. 4,467,129; 4,482,773 and EP 138 617 B. Other catalysts are based on mordenite and have been described in, for example, U.S. Pat. Nos. 4,723,051, 4,665,258 and FR 2,477,903.

Isomerization catalysts of C8-aromatic fractions that are based on EUO-structural-type zeolites, i.e., the EU-1, TPZ-3 and ZSM-50 zeolites, have been described by the applicant in Patent Applications FR 97/16,456 and 97/16,458.

Furthermore, the xylenes can be obtained by the transalkylation reactions of fractions that comprise toluene and aromatic hydrocarbons with 9 carbon atoms, as described in Patent FR 2,761,905 of the applicant, in the presence of a catalyst with a mordenite and binder base that comprises at least one metal that is selected from among the metals of groups VI, VIII and VII. Actually, the transalkylation/dismutation makes it possible to move methyl groups of the aromatic compounds with 9 carbon atoms to compounds such as toluene to obtain xylenes. When the catalyst has dealkylating properties, ethylbenzene can also be transformed into benzene.

Some aromatic fractions with 8 carbon atoms contain a large amount of ethylbenzene, which results in the use of processes that link the production of benzene and the production of paraxylene. It is known by U.S. Pat. No. 4,783,568 to combine the stages of separation of the xylenes, isomerization and transalkylation to transform the ethylbenzene of this type of feedstock.

Based on the variety of products that are introduced into the isomerization zone, however, it is important to be able to optimize the isomerization conditions of the isomers of the xylenes, and thereby to reduce the impurities and increase the paraxylene yield.

SUMMARY OF THE INVENTION

This invention relates to a scheme of three processes that have as their object to produce an isomer of xylenes starting from a feedstock that comprises aromatic compounds with 8 carbon atoms (C8), including ethylbenzene. The feedstock is treated in a zone for separating isomers of xylenes to extract the desired isomer, the raffinate that is low in desired isomer is sent into a zone for catalytic isomerization of the xylenes, the mixture that is obtained, which has a xylene composition that is close to the equilibrium composition and to which toluene and aromatic compounds with 9 carbon atoms (C9) are added, is sent into a catalytic transalkylation zone to recover, after treatment in at least one distillation zone, a fraction that is high in benzene, a fraction that is high in toluene that can be recycled at the inlet to the transalkylation zone, a fraction that is high in xylenes that is sent into the zone for separation of xylenes and a fraction that is high in aromatic compounds with 9 carbon atoms that can be recycled at the inlet to the transalkylation zone. The scheme according to the invention is characterized in that the isomerization catalyst comprises at least one EUO-structural-type zeolite, for example the EU-1 zeolite and at least one element of group VIII of the periodic table. In an implementation of the invention, the fraction that is high in benzene can be sent to a catalytic zone for alkylation of benzene with mono-olefins.

ADVANTAGE OF THE INVENTION

The process according to this invention makes it possible, surprisingly enough, to obtain paraxylene yields that are much higher than those of the prior art using improved performance levels in activity and selectivity during the isomerization stage, which also leads to a reduction of the recycling volumes as well as a reduction of the amount of catalyst that is necessary for the isomerization stage and for the transalkylation stage. Actually, the process according to this invention makes it possible to limit the losses during the isomerization stage, with the use of a catalyst that comprises an EUO-structural-type zeolite. In addition, the stability of the isomerization catalyst is improved relative to the catalysts of the prior art. Finally, the process according to the invention, which combines 3 stages, makes it possible to treat the feedstocks that comprise aromatic compounds with 8 carbon atoms with a large percentage of ethylbenzene, whereby the stages of isomerization and transalkylation make it possible to convert at least a portion of the ethylbenzene that is contained in the feedstock into benzene and xylenes, which makes it possible to increase the final benzene yield. The benzene that is produced with the process according to the invention then has high purity and can advantageously be used in a zone for alkylation of the benzene by mono-olefins for the synthesis of phenylalkanes (linear alkyl benzene, LAB).

DESCRIPTION OF THE INVENTION

The invention relates to a process for the production of at least one isomer of xylenes starting from a feedstock that comprises aromatic hydrocarbons with 8 carbon atoms per molecule, such as orthoxylene, metaxylene, paraxylene, and ethylbenzene, with a desired isomer yield that is improved relative to the process of the prior art with the use in the isomerization zone of a catalyst that comprises at least one EUO-structural-type zeolite.

The feedstock that is to be treated comprises xylenes and ethylbenzene. The process according to the invention advantageously makes it possible to convert feedstocks that comprise a large amount of ethylbenzene. Thus, the feedstocks that are to be treated are such that the ethylbenzene content relative to the overall content of aromatic compounds with 8 carbon atoms per molecule is greater than 25% by weight and even more preferably greater than 35% by weight. The feedstock can comprise any other compound, such as aromatic compounds with 9 carbon atoms, of toluene. It is possible to add these compounds to the feedstock in the form of fresh products or in the form of recycled products. The feedstock can be introduced into the separation zone of the xylenes when the feedstock comprises in large part xylenes and ethylbenzene. In the case where the feedstock contains C7- and C9-aromatic compounds, the feedstock can then be introduced, for example, directly into the transalkylation zone, where the conversion of the C7- and C9-aromatic compounds into xylenes takes place, whereby said xylenes are then sent into a zone for separating xylenes. Furthermore, the feedstock can be introduced into one of the distillation zones that treat the effluent resulting from transalkylation, based on the components of said feed stock.

The process according to the invention thus comprises the following stages:

a) The feedstock is introduced into at least one zone for separating xylenes, and a first fraction that is high in desired isomer and a second fraction that is low in desired isomer are recovered, said second fraction comprising the majority of the other isomers as well as the majority of the ethylbenzene, b) at least a portion of said fraction that is low in desired isomer and that is drawn off from the separation zone into at least one catalytic zone for isomerization of aromatic compounds with 8 carbon atoms is treated to convert at least a portion of the ethylbenzene into xylenes and to recover an effluent that comprises paraxylene, orthoxylene, metaxylene and ethylbenzene, c) a feedstock that comprises a portion of said effluent of the isomerization zone, aromatic hydrocarbons with 9 carbon atoms per molecule, of toluene, is treated in at least one catalytic transalkylation zone to recover an effluent that comprises benzene, toluene, C9-aromatic hydrocarbons, orthoxylene, paraxylene and metaxylene, d) the effluent of the transalkylation zone is treated in at least one distillation zone from which are drawn off a benzene-rich fraction, a toluene-rich fraction, a xylene-rich fraction and a fraction that contains C9-aromatic hydrocarbons, e) at least a portion of the xylene-rich fraction that is drawn off from the distillation zone is recycled in the zone for separating xylenes that is described in a).

The process according to the invention is characterized in that the catalyst that is used in the isomerization zone that is described in b) comprises at least one EUO-structural-type zeolite and at least one element of group VIII of the periodic table.

The catalyst that is used in the isomerization stage thus comprises at least one EUO zeolite, i.e., the EU-1, TPZ-3 and ZSM-50 zeolites.

The EUO-structural-type EU-1 zeolite, already described in the prior art, has a monodimensional microporous network, whose pore diameter is 4.1×5.7 Å (1 Å=1 angstrom=$1.10^{-10}$ m) ("Atlas of Zeolites Structure Types," W. M. Meier and D. H. Olson, 4th Edition, 1996). On the other hand, N. A. Briscoe et al. taught in an article in the Zeolites journal (1988, 8, 74) that these monodimensional channels have side pockets with a depth of 8.1 Å and a diameter of 6.8×5.8 Å. The synthesis mode of the EU-1 zeolite and its physico-chemical characteristics were described in the EP-B 1-42 226 patent.

U.S. Pat. No. 4,640,829 relates to the ZSM-50 zeolite, which, according to "The Atlas of Zeolites Structure Types," W. M. Meier and D. H. Olson, 4th Edition, 1996, has the EUO-structural type.

Patent EP-A1-51 318 relates to the TPZ-3 zeolite, which has the EUO-structural type according to "The Atlas of Zeolites Structure Types," W. M. Meier and D. H. Olson, 4th Edition, 1996.

The first stage of the process according to the invention comprises the treatment of the feedstock in a zone for separating xylenes.

The separation zone comprises at least one adsorption zone in which the majority of the desired isomer or the majority of the undesirable isomers are adsorbed. In an implementation of the invention, the separation zone makes it possible to recover the paraxylene, i.e., the paraxylene is adsorbed and recovered as an extract. Other implementations make it possible to recover the metaxylene and the orthoxylene as an extract based on the selected adsorbent. The adsorption zone operates in a simulated moving bed and comprises at least one zeolitic adsorbent bed that operates in the presence of a suitable desorption solvent and under adsorption conditions such that in the case where an effort is made to recover paraxylene, a first fraction that contains solvent, metaxylene, ethylbenzene and orthoxylene and a second fraction that contains solvent and basically paraxylene are obtained. The paraxylene that is obtained generally has a purity of between 75 and 99.9%. The first fraction is distilled to separate the solvent, on the one hand, and the metaxylene, orthoxylene and ethylbenzene mixture, on the other hand, and the second fraction is also distilled to recover the paraxylene, on the one hand, and the solvent, on the other hand. The first fraction is then sent into the zone for isomerization of aromatic alkyls. The solvent can be recycled at the inlet of the separation zone.

The simulated moving bed can be a simulated counter-current bed or a simulated co-current bed.

The solvent of elution or desorption is selected from among toluene and paradiethylbenzene. Other solvents such as methyl tert-butyl ether (MTBE) or diisopropyl ether (DIPE) can also be used.

The specific adsorbents of the paraxylene comprise at least one zeolite that is selected from among the X, Y zeolites, whose exchangeable sites are occupied by at least one alkaline cation or alkaline-earth cation, such as, for example, barium and potassium.

The adsorbents that make it possible to absorb selectively the metaxylene and the orthoxylene are, for example, the Y zeolites that are exchanged with at least one element that is selected from among Li, Na, Be, Mg, Ca, Sr, Mn, Cd, Cu, Ni to obtain a raffinate that comprises the paraxylene.

In a particular implementation, the xylene separation zone comprises a crystallization zone downstream from the adsorption zone. Thus, for example, the paraxylene that is recovered after distillation of said second fraction is sent into a crystallization zone at a temperature of between +10 and −25° C., and, on the one hand, a mother liquor that is recycled to the adsorption zone is obtained, and, on the other hand, paraxylene crystals that are saturated with mother liquor are obtained, then paraxylene crystals with a very high degree of purity, or generally purity greater than 99.3% and preferably greater than 99.7%, are washed with a suitable washing solvent.

As a solvent for washing crystals, it is possible to use, for example, n-pentane, water, purified paraxylene or toluene. Preferably, either the same solvent for the desorption and for the washing of crystals, such as for example, toluene, is used, or a fraction of purified paraxylene is used.

The first distilled fraction that is recovered after the stage for separating xylenes that comprises orthoxylene, metaxylene and ethylbenzene is treated in an isomerization zone. The isomerization stage is used in the presence of a catalyst that comprises an EUO-structural-type zeolite, for example the EU-1 zeolite. The EUO-structural-type zeolite is at least in part in acid form and comprises silicon and at least one T element that is selected from the group that is formed by aluminum, iron, gallium and boron, preferably aluminum, with an overall Si/T atomic ratio that is greater than 5.

The catalyst also comprises at least one matrix that comprises at least one compound that is selected from the group that is formed by clays, magnesia, aluminas, silicas, titanium oxide, boron oxide, zirconia, aluminum phosphates, titanium phosphates, zirconium phosphates and silica-aluminas. Preferably, the matrix is alumina. The catalyst comprises at least one element of group VIII of the periodic table, preferably selected from among platinum and palladium, and can also optionally contain at least one metal that is selected from among the metals of groups IIIA and IVA, preferably selected from among tin and indium and optionally sulfur.

The isomerization catalyst comprises by weight relative to the total catalyst mass:

from 1 to 90% by weight of at least one EUO-structural-type zeolite, preferably 3 to 60% and even more preferably 4 to 40%, from 0.01 to 2% by weight of at least one metal of group VIII, preferably 0.05 to 1%, optionally from 0.01 to 2% of at least one additional element that is selected from groups IIIA and IVA of the periodic table, preferably 0.05 to 1%, optionally sulfur, a binder that ensures the addition by weight to 100% of the catalyst.

According to a preferred embodiment of the invention, a catalyst will be used that comprises an EUO-structural-type zeolite whose crystal size is less than 5 micrometers ($\mu$m), preferably less than 0.5 $\mu$m, and even more preferably less than 0.2 $\mu$m. These crystals or crystallites are often grouped in aggregates that have a grain size such that the value of Dv.90 is less than or equal to 500 $\mu$m, often less than 400 $\mu$m and most often less than 200 $\mu$M and preferably less than 50 $\mu$m. The size of the aggregates is determined by grain size with laser diffraction. This measurement is carried out on the zeolite powder that is suspended in water. After a first measurement, the suspension is subjected to ultrasonic waves for thirty seconds, and then a new measurement is carried out. The ultrasonic waves that are used are characterized by a power of 50 W and a frequency of 50 kHz. This procedure is repeated until the result no longer varies (at ±5%). The size distribution of the aggregates that is defined by volume is calculated starting from light signals that are collected by the detectors and with the Fraunhofer theory. Dv,X is defined as being the equivalent sphere diameter such that X% by volume of the aggregates has a size that is smaller than said diameter. These characteristics will be obtained directly during the synthesis of the zeolite and/or by any method that makes it possible to reduce the size of the aggregates such as, for example, the post-synthesis grinding or else a suitable mixing before shaping.

The catalyst is preferably prepared as described in the patent application of the applicant FR 97/16,456, incorporated here with reference. Thus, the catalyst preferably has a metal dispersion of group VIII that is between 50 and 100% and more preferably between 60 and 100% and even more preferably between 70 and 100%, whereby a macroscopic distribution coefficient of said metal of group VIII is between 0.7 and 1.3, and preferably between 0.8 and 1.2. Preferably, the catalyst is shaped in the form of balls or extrudates and has a mechanical resistance such that the bed crushing value is greater than 0.7 MPa.

The isomerization zone is operated at a temperature of about 300° C. to 500° C., preferably about 320° C. to 450° C. and even more preferably about 350° C. to 420° C., at a partial hydrogen pressur 0.3 to 1.5 MPa, preferably about 0.4 to 1.2 MPa, at a total pressure of about 0.45 to 1.9 NPa, preferably about 0.6 to 1.5 MPa, at a PPH (feedstock weight/catalyst weight/hour) of about 0.25 h−1 to 30 h−1, preferably about 1 to 10 h−1, and very often 2 h−1 to 7 h−1. The hydrogen that is introduced for carrying out isomerization can be recycled in said isomerization zone.

In a particular implementation of the isomerization stage, the isomerization zone comprises a recycling as described in the patent application of the applicant FR 98/04 526, incorporated here with reference. The process then comprises at least one distillation zone between the isomerization zone and the transalkylation zone, to recover, after the fraction that comprises the light compounds (with a boiling point less than 80° C.) is eliminated, a fraction that contains in large part the aromatic compounds that contain at least 8 carbon atoms per molecule and that is sent into the transalkylation zone to recover a fraction that comprises at least one compound with a boiling point of about 80° C. to 135° C. and more particularly at least one of the compounds that is selected in the group that consists of naphthenes with 8 carbon atoms per molecule, the paraffins with 8 carbon atoms per molecule, benzene and toluene, at least one of the compounds of said fraction, isolated from the entire fraction by treatment in at least one distillation zone that can be recycled at the inlet of the isomerization zone.

The mass percentage of recycled compounds relative to the total feedstock that enters the isomerization zone is between 0.01 and 20%. Actually, surprisingly enough, the fact of recycling at least one compound with a boiling point of between 80° C. and 135° C. makes it possible to reduce the parasitic reactions of the isomerization and, moreover, makes it possible to reduce the volume of the feedstock of the transalkylation zone, which, combined with the performance levels of the catalyst according to the invention, ensures considerable savings for the device. The naphthenes are preferably recycled in the isomerization zone, whereby the other compounds of the fraction with a boiling point of between 80° C. and 135° C. such as toluene and the paraffins can be recovered at this level of the process.

The effluent resulting from the isomerization zone that comprises the three isomers of xylenes in a ratio that is basically close to that of the thermodynamic equilibrium and that comprises ethylbenzene is then sent into a catalytic transalkylation zone. Aromatic compounds with 9 carbon atoms are added to the feedstock of the transalkylation zone of the toluene either by recycling or by adding fresh products. The transalkylation zone makes it possible both to transform the C9-aromatic compounds and the C7-aromatic compounds such as toluene into xylenes and to dealkylate the majority of the ethylbenzene into benzene and therefore to convert the majority of the ethylbenzene that is present in the feedstock into benzene while obtaining a total paraxylene yield that is improved relative to the processes of the prior art.

The transalkylation stage can be used in the presence of any catalyst that is known to one skilled in the art. In particular, it is possible to use a catalyst based on mordenite and at least one metal of group VIIB of the periodic table, such as, for example, rhenium. The catalyst can also contain at least one element that is selected from groups VIII, IVB, III and VIB of the periodic table, preferably at least one element that is selected from groups IVB and VIII, preferably selected from among nickel and tin.

In general, the catalyst comprises 40 to 90% by weight of mordenite zeolite that has an Si/Al ratio that is greater than 35, from 0.01 to 5% by weight of at least one metal of group VIIB, whereby the addition by weight consists of binder, selected from among, for example, clays, magnesia, aluminas, silicas, titanium oxide, boron oxide, zirconia, aluminum phosphates, titanium phosphates, zirconium phosphates and silica-aluminas. Preferably the binder is alumina.

Surprisingly enough, the transalkylation catalyst of this invention makes possible the transalkylation of the aromatic compounds and also the dealkylation of the aromatic compounds, such as, for example, the ethylbenzene, to obtain benzene in a large amount and therefore to convert the majority of the ethylbenzene that is present in the feedstock.

The transalkylation zone is used at a temperature of between 250 and 600° C., preferably between 330 and 500° C., under a pressure of between 1 and 6 MPa, preferably between 2 and 4.5 MPa, with a PPH that is expressed by kilogram of feedstock that is introduced per kilogram of catalyst and per hour, between 0.1 h$^{-1}$ and 10 h$^{-1}$ and preferably between 0.5 and 4; a hydrogen to hydrocarbon molar ratio of between 2 and 20 and preferably between 3 and 12. The hydrogen that is introduced for the transalkylation can be recycled in the transalkylation zone.

The effluent of the transalkylation zone that comprises 3 isomers of xylenes with a composition that is close to the one at equilibrium, benzene, a small amount of ethylbenzene, toluene and aromatic compounds with 9 carbon atoms per molecule that are not transformed is then freed of its lightest components that comprise up to 6 carbon atoms per molecule, whereby the bottom effluent is then fractionated by treatment in at least one distillation zone to recover a fraction that comprises in large part benzene, a fraction that comprises in large part toluene, whereby said fraction can be at least partly recycled to the transalkylation zone, a fraction that comprises in large part xylenes and a small amount of ethylbenzene that is sent at least partly into the zone for separating xylenes, a fraction that comprises in large part aromatic compounds with 9 carbon atoms that can be at least partly recycled into the transalkylation zone. The process preferably comprises at least one zone for separate distillation by recovered fraction. Thus, the process preferably comprises a distillation zone for recovering light compounds, a distillation zone for recovering benzene, a distillation zone for recovering toluene, a distillation zone for recovering xylenes, a distillation zone for recovering C9-aromatic compounds.

The fraction that comprises in large part the aromatic compounds with 8 carbon atoms is then sent as a feedstock into the zone for separating xylenes to which it is possible to add a feedstock as defined above.

In a particular implementation of the invention, the benzene that is produced will be sent into a reactor that contains a suitable catalyst for the production of phenylalkanes with alkylation by mono-olefins. The aromatic alkylation stage can be carried out in the presence of any catalyst that is known to one skilled in the art. It is possible to use an acid-type catalyst such as HF or a Friedel-Craft-type catalyst, in particular with an AlCl3 base. It is also possible to use solid catalysts based on cancrinite, gmelinite, mordenite, offretite, ZSM-12 or EUO catalysts.

In the case of a zeolitic catalyst, a catalyst with an EUO zeolite base, such as EU-1, shaped with a binder such as alumina, is preferably used.

During the alkylation stage, the benzene that is obtained from the effluent of the transalkylation is preferably reacted in a reaction zone with a feedstock that contains at least one linear olefin that comprises 9 to 16 carbon atoms per molecule, preferably 10 to 14 carbon atoms per molecule, in contact with a catalyst based on an EUO-structural-type zeolite that has the characteristics defined above, then the product that is obtained is fractionated to collect separately a first fraction that contains unconverted benzene, a second fraction that contains at least one unconverted C9–C16 linear olefin (preferably C10–C14), a third fraction that contains 2-, 3-, 4-, 5- and 6-phenylalkanes and a fourth fraction that contains at least one poly-alkylbenzene (or poly-alkylbenzene fraction), whereby the latter is then at least partly recycled to said zone for alkylating benzene where it therefore reacts with benzene in contact with said catalyst to be transalkylated at least in part, and a mixture of 2-, 3-, 4-, 5- and 6-phenylalkanes is collected.

Thus, the reactions for alkylation of benzene and for migration of the alkyl groups to the benzene core take place together in the same reaction zone (i. e, in the same reactor) in the presence of the same catalyst. The first fraction that contains unconverted benzene is preferably at least partly recycled to said reaction zone. Likewise, preferably the second fraction that contains at least one unconverted C9–C16 linear olefin (usually C10–C14) is at least partly recycled to said reaction zone.

The recycled portion of the fourth fraction preferably contains basically at least one dialkylbenzene and is preferably essentially free of heavy alkyl-aromatic compounds that optionally can be eliminated by fractionation.

This variant of the invention can be carried out at a temperature that is less than 300° C., for example less than 60° C., under a pressure of 1 to 10 MPa, with a liquid hydrocarbon flow rate (volumetric flow rate) of about 0.5 to 50 volumes per volume of catalyst and per hour and with a benzene/olefin molar ratio of between 1 and 20.

Figure 1:
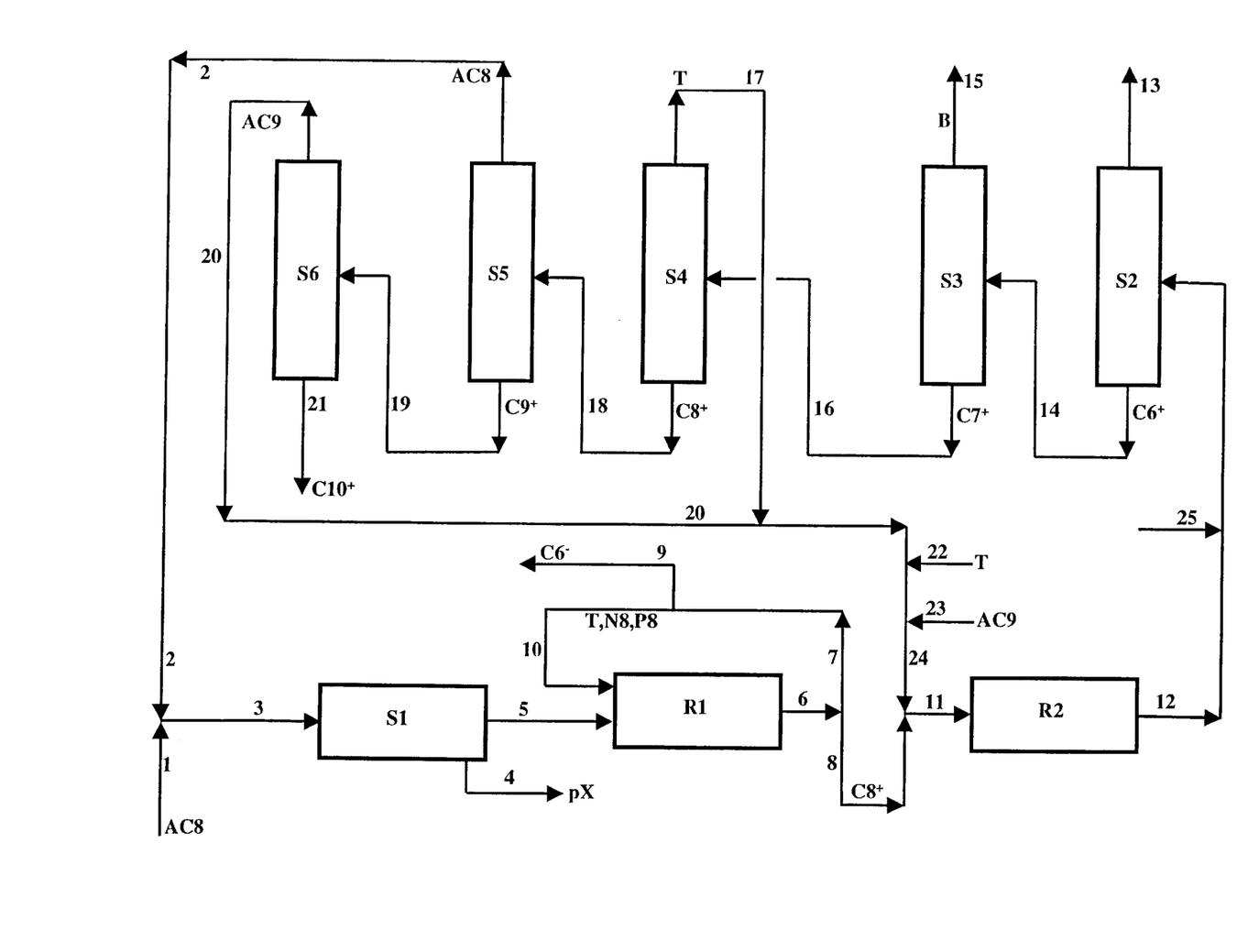
FIG. 1 illustrates the invention, without representation of the use of benzene in an aromatic alkylation zone.

An aromatic hydrocarbon feedstock (1) that contains ethylbenzene, paraxylene, orthoxylene and metaxylene is introduced with a recycled transalkylation effluent (2) via line (3) into a zone for separating xylenes S1 in the presence of an elution solvent.

A raffinate that is low in desired isomer, for example paraxylene, and that contains basically solvent, ethylbenzene and undesirable isomers, for example orthoxylene and metaxylene, is drawn off via line (5), and an extract that is high in desired isomer, for example paraxylene, is drawn off via line (4).

Raffinate (5), freed of solvent by a means not shown in the figure, is sent with a recycled isomerization effluent that comprises at least one compound that is selected from among toluene, C8-naphthenes and C8 paraffins (10) into an isomerization zone of R1 xylenes. Isomerate (6) is separated into a heavy fraction (8) that comprises the aromatic compounds that have at least 8 carbon atoms per molecule and a light fraction (7) from which compounds that have less than 6 carbon atoms (9) are removed, whereby residual effluent (10) that comprises at least one compound that is selected from among toluene, naphthenes and paraffins is at least partly recycled into the isomerization zone.

The fraction that comprises the aromatic compound that has at least 8 carbon atoms (8) is mixed with C9-aromatic compounds and toluene that are obtained from either making up ((22), (23)); or a recycling of fractions of transalkylation effluent ((17), 20)) in a transalkylation zone R2, via line 11.

The effluent of the transalkylation zone is sent via line 12 into a separation string that comprises a first distillation S2 that makes it possible to eliminate C6-light compounds (13), whereby fraction C6 at the bottom of column (14) is sent into a second distillation zone (S3) which makes it possible to collect benzene of high purity (15), which can be sent to a zone for alkylation of benzene (not shown in the figure) via the mono-olefins, whereby fraction C7* at the bottom of column (16) is sent into a third distillation zone (S4), which makes it possible to collect toluene (17) that is sent to the inlet of transalkylation zone (R2), whereby the C8* fraction at the bottom of column (18) is sent into a fourth distillation zone (S5) that makes it possible to collect an aromatic fraction with 8 carbon atoms (2) recycled to the zone for separating xylenes (S1), whereby fraction C9* at the bottom of column (19) is sent into a fifth distillation zone (S6) that makes it possible to collect an AC9 (20) fraction that is recycled at the inlet of transalkylation zone (R2), whereby the C10+ fraction at the bottom of the column is eliminated (21).

EXAMPLES

Example According to the Invention

The following example that illustrates the invention is carried out according to FIG. 1.

The fresh feedstock of aromatic hydrocarbons (1) has the following composition (% by weight):

| | |
|---|---|
| Ethylbenzene | 45.0 |
| p-Xylene | 13.9 |
| m-Xylene | 27.3 |
| o-Xylene | 13.8 |

The treated mixture in the zone for separating xylenes (S1) consists of 20% by weight of fresh feedstock (1) and 80% by weight of aromatic compounds with 8 carbon atoms that are obtained from the effluent of transalkylation zone (2).

At the inlet to separation zone (3), the aromatic compounds with eight carbon atoms are in the following proportions (% by weight):

| | |
|---|---|
| Ethylbenzene | 11.3 |
| p-Xylene | 21.6 |
| m-Xylene | 46.1 |
| o-Xylene | 21.1 |

The separation of paraxylene (S1) takes place under the following condiions:

desorption in a simulated countercurrent moving bed (stand-alone version):

| | |
|---|---|
| Sieve | Ba-X; 5.5% $H_2O$ measured by loss due to ignition (LOI) at 950° C. |
| Temperature | 170° C. |
| Number of beds | 24 |
| Minimum pressure | 9 bar |
| PDEB/feedstock ratio | 1.5:1 |
| Productivity | 69.8 kg of pX/$m^3$ of sieve/hour |

The paraxylene that is recovered as extract (4) has a purity of 99.8% and a yield of 95.4% or 20.6% by weight of paraxylene that is collected relative to the feedstock that is treated in the separation zone.

Raffinate (5), after distillation of the desorption solvent (separation not shown in the figure), has the following composition (% by weight):

| | |
|---|---|
| Ethylbenzene | 14.2 |
| p-Xylene | 1.3 |
| m-Xylene | 58.0 |
| o-Xylene | 26.5 |

This raffinate (5), mixed with the naphthenes with 8 carbon atoms as well as the paraffins with 8 carbon atoms and toluene that are obtained from the isomerization reactor and recycled (10), is isomerized in isomerization zone (R1) under the following conditions:

Catalyst: Pt/EU-1 zeolite of the Si/Al ratio 18/binder (alumina) (0.3%/10%/89.7%)

Temperature: 380° C.

$H_2$ hydrocarbons/ratio: 4:1

Pressure: 8 bar

Isomerization effluent (6) has the following composition (% by weight):

| | |
|---|---|
| C6- | 0.8 |
| Benzene | 0.1 |
| Toluene | 1.1 |
| 8C Paraffins | 0.3 |
| 8C Naphthenes | 8.6 |
| Ethylbenzene | 8.7 |
| p-Xylene | 18.7 |
| m-Xylene | 41.4 |
| o-Xylene | 19.7 |
| AC9 | 0.5 |

The isomerization catalyst that is based on EU-1 zeolite therefore made it possible to convert 39% by weight of ethylbenzene, and the yield of the isomerization zone, in aromatic compounds with 8 carbon atoms+naphthenes with 8 carbon atoms, is 98%.

This isomerate is sent into a separation zone (not shown in the figure) that makes it possible to eliminate (C6-) light compounds (9) and to separate the fraction that contains the toluene as well as the naphthenes and paraffins with 8 carbon atoms (10). This fraction is recycled at the inlet to the isomerization reactor which makes it possible to eliminate the losses of aromatic compounds with 8 carbon atoms in the form of naphthenes by hydrogenation reactions, whereby these reactions are balanced under the operating conditions that are applied.

The volume of the recycling in isomerization corresponds to 9.1% by weight of the feedstock that comes into the isomerization reactor and the net losses (non-recyclable compounds) are 0.9% by weight.

The AC8+ mixture that is collected after separation (8) has the following composition (% by weight):

| | |
|---|---|
| Ethylbenzene | 9.8 |
| p-Xylene | 21.1 |
| m-Xylene | 46.5 |
| o-Xylene | 22.2 |
| AC9 | 0.6 |

This effluent is sent to transalkylation zone (R2) and mixed with toluene and aromatic compounds with 9 carbon atoms (24) that are obtained either from makeup (22, 23) or the separation chain of the transalkylation effluent and recycled (17,20).

In the example that is described, the AC8+ that are obtained from the isomerization zone are treated mixed with toluene and AC9 in ratios by weight of 60/20/20.

Feedstock (11) that arrives at the inlet to transalkylation reactor (R2) therefore has the following composition (% by weight):

| | |
|---|---|
| Toluene | 20 |
| Ethylbenzene | 5.9 |
| p-Xylene | 12.6 |
| m-Xylene | 27.9 |
| o-Xylene | 13.3 |
| AC9 | 20.4 |

This feedstock is treated in transalkylation reactor (R2) under the following conditions:
Catalyst: rhenium/mordenite/alumina (0.29%/79.8%/19.9%)
Temperature: 400° C.
$H_2$/hydrocarbon ratio: 5:1
Pressure: 30 bar
Effluent (12) that is obtained from the transalkylation zone has the following composition (% by weight):

| | |
|---|---|
| C6- | 4.8 |
| Benzene | 6.3 |
| Toluene | 14.9 |
| Ethylbenzene | 1.8 |
| p-Xylene | 14.8 |
| m-Xylene | 32.0 |
| o-Xylene | 14.4 |
| AC9 | 8.5 |
| AC10+ | 2.5 |

The conversion of the ethylbenzene is 70% by weight in the transalkylation zone.

This transalkylation effluent (12) is sent into a separation train:

First distillation (S2) makes it possible to eliminate (C6-) light compounds (13), and the C6+ fraction at the bottom of column (14) is sent into a second column (S3), second distillation (S3) makes it possible to collect high-purity benzene (15), and the C7+ fraction at the bottom of column (16) is sent into a third column (S4), third distillation (S4) makes it possible to collect toluene (17) that is recycled at the inlet to transalkylation reactor (R2), and the C8+ fraction at the bottom of column (18) is sent into a fourth column (S5), fourth distillation (S5) makes it possible to collect an AC8 fraction (2) that is recycled to separation zone (S1), and the C9+ fraction at the bottom of column (19) is sent into a fifth column (S6), fifth distillation (S6) makes it possible to collect an AC9 fraction (20) that is recycled at the inlet to transalkylation reactor (R2), and the C10+ fraction at the bottom of column (21) is eliminated.

Overall, between the inlet to separation zone (S1) and the outlet to transalkylation zone (R2), the ethylbenzene is converted to 74.7% by weight.

For 100 kg of treated feedstock in the separation zone, there is a paraxylene yield of 20.6 kg and a benzene yield of 8.3 kg.

Comparative Example (Not in Accordance with this Invention)

To compare the performance levels that are obtained in terms of paraxylene yield and in terms of conversion of ethylbenzene from the entire process scheme, the same fresh feedstock as the one described in the preceding example that illustrates the invention is treated.

The treated mixture in the zone for separating xylenes (S1) consists of 20% by weight of fresh feedstock (1) and 80% by weight of aromatic compounds with 8 carbon atoms obtained from the effluent of transalkylation zone (2) as in the preceding example, to compare the performance levels that are obtained with the iso-quantity of treated fresh feedstock.

At the inlet to separation zone (3), the aromatic compounds with eight carbon atoms are in the following ratios (% by weight):

| | |
|---|---|
| Ethylbenzene | 12.0 |
| p-Xylene | 19.5 |
| m-Xylene | 48.0 |
| o-Xylene | 20.5 |

The separation of paraxylene (S1) takes place under the same conditions as in the example above according to the invention.

The productivity is 62.1 kg of pX/m3 of sieve/hour.

The paraxylene that is recovered as extract (4) has a purity of 99.8% and a yield of 90.1% or 17.6% by weight of paraxylene relative to the feedstock that is treated in the separation zone.

Raffinate (5), after distillation of the desorption solvent (separation that is not shown in the figure), has the following composition (% by weight):

| | |
|---|---|
| Ethylbenzene | 14.5 |
| p-Xylene | 2.3 |
| m-Xylene | 58.3 |
| o-Xylene | 24.9 |

This raffinate (5), mixed with the naphthenes with 8 carbon atoms as well as the paraffins with 8 carbon atoms and the toluene that are obtained from the isomerization reactor and recycled (10), is isomerized in isomerization zone (R1) under the same operating conditions as in the preceding example according to the invention but in the presence of a catalyst with a mordenite base:

Catalyst: Pt/mordenite/binder (alumina) (0.29%/15%/84.7%).

To be able to treat the feedstock under the same operating conditions, the catalytic volume had to be increased because the amount of feedstock to be treated is larger, whereby the amount of extracted paraxylene is smaller. Also, the volume of the recycling in isomerization is larger as will be seen in the example below, which also leads to an increase of the catalytic volume.

Overall, the amount of catalyst that is used should be increased by 5.0% by weight relative to the preceding example.

Isomerization effluent (6) has the following composition (% by weight):

| | |
|---|---|
| C6− | 0.8 |
| Benzene | 0.3 |
| Toluene | 1.4 |
| 8C Paraffins | 0.4 |
| 8C Naphthenes | 8.7 |
| Ethylbenzene | 9.2 |
| p-Xylene | 16.8 |
| m-Xylene | 42.0 |
| o-Xylene | 18.9 |
| AC9 | 1.4 |

The conversion of the ethylbenzene of the isomerization zone is therefore 36.6%, and the yield of aromatic compounds with 8 carbon atoms +naphthenes with 8 carbon atoms is 96.4%.

This isomerate is sent into a separation zone (not shown in the figure) that makes it possible to eliminate (C6−) light compounds (9) and to separate the fraction that contains toluene as well as naphthenes and paraffins with 8 carbon atoms (10). This fraction is recycled at the inlet to the isomerization reactor, which makes it possible to eliminate the losses of aromatic compounds with 8 carbon atoms in the form of naphthenes by hydrogenation reactions, whereby these reactions are balanced under the operating conditions that are applied.

The volume of recycling in the isomerization corresponds to 11.3% by weight of the feedstock that enters the isomerization reactor, and the net losses (non-recyclable compounds) are 1.1% by weight.

The AC8+ mixture that is collected after separation (8) has the following composition (% by weight):

| | |
|---|---|
| Ethylbenzene | 10.4 |
| p-Xylene | 19.1 |
| m-Xylene | 47.5 |

-continued

| | |
|---|---|
| o-Xylene | 21.4 |
| AC9 | 1.6 |

This effluent is sent to transalkylation zone (R2) and mixed with toluene and aromatic compounds with 9 carbon atoms (24) that are obtained either from makeup (22, 23) or the chain for separation of the transalkylation effluent and recycled (17, 20).

The AC8+ that are obtained from the isomerization zone are treated in a mixture with toluene and AC9 in proportions by weight of 60/20/20 that are identical to the preceding example according to the invention. The AC8+ amount that is obtained from the isomerization zone is larger which causes an increase of the catalytic volume of the transalkylation zone of 3.5% by weight to treat the feedstock under the same conditions.

Feedstock (11) that arrives at the inlet to transalkylation reactor (R2) therefore has the following composition (% by weight):

| | |
|---|---|
| Toluene | 20.0 |
| Ethylbenzene | 6.3 |
| p-Xylene | 11.4 |
| m-Xylene | 28.6 |
| o-Xylene | 12.9 |
| AC9 | 20.9 |

This feedstock is treated in transalkylation reactor (R2) under the same conditions as the preceding example according to the invention.

Effluent (12) that is obtained from the transalkylation zone has the following composition (% by weight):

| | |
|---|---|
| C6− | 4.9 |
| Benzene | 6.5 |
| Toluene | 15.1 |
| Ethylbenzene | 2.2 |
| p-Xylene | 13.0 |
| m-Xylene | 33.1 |
| o-Xylene | 13.8 |
| AC9 | 8.7 |
| AC10+ | 2.6 |

The conversion of the ethylbenzene is 65% by weight in the transalkylation zone.

This transalkylation effluent (12) is sent into a separation train:

First distillation (S2) makes it possible to eliminate (C6−) light compounds (13), and the C6+ fraction at the bottom of column (14) is sent into a second column (S3), second distillation (S3) makes it possible to collect high-purity benzene (15), and the C7+ fraction at the bottom of column (16) is sent into a third column (S4), third distillation (S4) makes it possible to collect toluene (17) that is recycled at the inlet to transalkylation reactor (R2), and the C8+ fraction at the bottom of column (18) is sent into a fourth column (S5), fourth distillation (S5) makes it possible to collect an AC8 fraction (2) that is recycled to separation zone (S1), and the C9+ fraction at the bottom of column (19) is sent into a fifth column (S6), fifth distillation (S6) makes it possible to collect an AC9 fraction (20) that is recycled at the inlet to transalkylation reactor (R2), and the C10+ fraction at the bottom of column (21) is eliminated.

Overall, between the inlet to separation zone (S1) and the outlet to transalkylation zone (R2), the ethylbenzene is converted to 69.1%.

For 100 kg of treated feedstock in the separation zone, there is a paraxylene yield of 17.5 kg and a benzene yield of 8.7 kg.

The amount of isomerization catalyst that is necessary for treating the same amount of feedstock is 5% by weight larger, and the amount of transalkylation catalyst is 3.5% by weight larger. In addition, the volume of the recycling in isomerization is increased by 24%, which is a major drawback as far as the device is concerned.

What is claimed is:

1. A process for the production of at least one isomer of xylene from an aromatic hydrocarbon feedstock with 8 carbon atoms per molecule that comprises orthoxylene, metaxylene, paraxylene, and the ethylbenzene:
   a) introducing the feedstock into at least one zone for separating xylenes, and recovering a first fraction that is high in desired isomer and a second fraction that is low in desired isomer, comprising the majority of other isomers and ethylbenzene,
   b) treating at least a portion of said fraction that is low in desired isomer in at least one catalytic zone for isomerization of aromatic compounds with 8 carbon atoms to convert at least a portion of the ethylbenzene into xylenes and recovering an effluent that comprises paraxylene, orthoxylene, metaxylene and ethylbenzene,
   c) treating a feedstock that comprises at least a portion of said effluent of the isomerization zone, aromatic hydrocarbons with 9 carbon atoms per molecule, and toluene, in at least one catalytic transalkylation zone, to recover an effluent that comprises benzene, toluene, C9-aromatic hydrocarbons, orthoxylene, paraxylene and metaxylene,
   d) distilling the effluent of the transalkylation zone in at least one distillation zone and drawing off a benzene-rich fraction, a toluene-rich fraction, a xylene-rich fraction and a fraction that contains C9-aromatic hydrocarbons,
   e) recycling at least a portion of the xylene-rich fraction from the distillation zone to the zone for separating xylenes in a),
   wherein the catalyst that is used in the isomerization zone b) comprises at least one EUO-structural elite whose crystals are grouped in aggregates that have a grain size with a value of dv,90 less than or equal to 400 microns and at least one metal of group VIII of the periodic table.

2. A process according to claim 1, such that the desired xylene isomer is paraxylene.

3. A process according to claim 1, such that the desired xylene isomer is metaxylene.

4. A process according to claim 1, such that the feedstock in a) comprises at least 25% by weight of ethylbenzene.

5. A process according to claim 1, such that at least a portion of the toluene and/or at least a portion of the aromatic hydrocarbons with 9 carbon atoms that is drawn off from the distillation zone that is described in stage d) is recycled at the inlet to the transalkylation zone that is described in c).

6. A process according to claim 1, such that the catalyst that is used in the isomerization zone that is described in b) has a base of at least one EUO zeolite that is EU-1, TPZ-3, or ZSM-50 zeolite each comprising silicon and at least one T element that is aluminum, iron, gallium or boron, with an overall Si/T ratio that is greater than 5.

7. A process according to claim 1, such that the crystals of the EUO zeolite of the catalyst of the isomerization zone that is described in b) is less than 5 $\mu$m in size.

8. A process according to claim 1, such that the catalyst that is used in the isomerization zone that is described in b) also comprises at least one metal of groups IIIA and IVA.

9. A process according to claim 1, such that the catalyst that is used in the isomerization zone that is described in b) has a dispersion of the metal of group VIII of between 50 and 100%.

10. A process according to claim 1, such that the catalyst that is used in the isomerization zone that is described in b) has a macroscopic distribution coefficient of the metal of group VIII of between 0.7 and 1.3.

11. A process according to claim 1, such that the catalyst in b) is shaped in the form of balls or extrudates and has a mechanical resistance such that the bed crushing value is greater than 0.7 MPa.

12. A process according to claim 1, such that the isomerization zone that is described in b) is operated at a temperature of between 300 and 500° C., at a partial hydrogen pressure of between 0.3 and 1.5 MPa, at a total pressure of between 0.45 and 1.9 MPa, and with a pph (feedstock weight/catalyst weight/hour) of between 0.25 $h^{-1}$ and 30 $h^{-1}$.

13. A process according to claim 1, such that at least one fraction of the effluent resulting from isomerization, whereby said fraction comprises at least one compound with a boiling point of between 80 and 135° C., is recycled in the isomerization zone that is described in b).

14. A process according to claim 1, such that the catalyst that is used in the transalkylation zone that is described in c) has a mordenite base and comprises at least one metal of group VIIB of the periodic table.

15. A process according to claim 1, such that the catalyst that is used in the transalkylation stage that is described in c) also comprises at least one element that is selected from groups IVB and VIII of the periodic table.

16. A process according to claim 1, such that the transalkylation stage that is described in c) is operated at a temperature of between 250° C. and 600° C. under a pressure of between 1 and 6 MPa, with a PPH of between 0.1 h–1 and 10 h–1, with a hydrogen to hydrocarbon molar ratio of between 2 and 20.

17. A process according to claim 1, such that the zone for separating xylenes that is described in a) is an adsorption zone of a simulated moving bed in the presence of a zeolitic sieve.

18. A process according to claim 17, such that the zeolitic sieve comprises at least one zeolite from among the X, Y zeolites, whose exchangeable sites are occupied by at least one alkaline cation or alkaline-earth cation.

19. A process according to claim 17, such that the zeolitic sieve comprises a Y zeolite that is exchanged with at least one element that is selected from among Li, Na, Be, Mg, Ca, Sr, Mn, Cd, Cu, Ni.

20. A process according to claim 17, such that adsorption takes place in the presence of an elution solvent that is selected from among toluene, paradiethylbenzene, MTBE, and methyl isopropyl ether.

21. A process according to claim 17, such that the separation zone comprises a crystallization zone downstream from the adsorption.

22. A process according to claim 1, such that the benzene that is drawn off from the distillation zone that is described in d) is sent into a catalytic reaction zone for alkylation of benzene with mono-olefins to produce phenylalkanes.

23. A process according to claim 22 wherein the catalyst that is used in the zone for alkylating benzene by mono-olefins is an acid catalyst, a Friedel-Craft catalyst, or a solid catalyst with a zeolite base.

24. In a process for the production of at least one isomer of xylene from an aromatic hydrocarbon feedstock with 8 carbon atoms per molecule and comprising orthoxylene, metaxylene, paraxylene and ethylbenzene, said process comprising separating a desired xylene isomer, isomerizing non-desired isomers to produce desired isomers, and transalkylating isomerization effluent, $C_9$-aromatic hydrocarbons and toluene to produce xylene isomers, the improvement wherein the isomerization is conducted in the presence of at least one EUO-structural zeolite whose crystals are grouped in aggregates that have a grain size with a value of dv,90 less than or equal to 400 microns and at least one group VIII metal.

25. A process according to claim 23, wherein the catalyst used in the zone for alkylating benzene is hydrofluoric acid, aluminum chloride, EUO zeolite, cancrinite, gmelinite, mordenite, offretite or ZSM-12 zeolite.

26. A process for the production of at least one isomer of xylene from an aromatic hydrocarbon feedstock with 8 carbon atoms per molecule that comprises orthoxylene, metaxylene, paraxylene, and the ethylbenzene:

a) introducing the feedstock into at least one zone for separating xylenes, and recovering a first fraction that is high in desired isomer and a second fraction that is low in desired isomer, comprising the majority of other isomers and ethylbenzene, b) treating at least a portion of said fraction that is low in desired isomer in at least one catalytic zone for isomerization of aromatic compounds with 8 carbon atoms to convert at least a portion of the ethylbenzene into xylenes and recovering an effluent that comprises paraxylene, orthoxylene, metaxylene and ethylbenzene, c) treating a feedstock that comprises at least a portion of said effluent of the isomerization zone, aromatic hydrocarbons with 9 carbon atoms per molecule, and toluene, in at least one catalytic transalkylation zone, to recover an effluent that comprises benzene, toluene, C9-aromatic hydrocarbons, orthoxylene, paraxylene and metaxylene, d) distilling the effluent of the transalkylation zone in at least one distillation zone and drawing off a benzene-rich fraction, a toluene-rich fraction, a xylene-rich fraction and a fraction that contains C9-aromatic hydrocarbons, e) recycling at least a portion of the xylene-rich fraction from the distillation zone to the zone for separating xylenes in a), wherein the catalyst that is used in the isomerization zone b) comprises at least one EUO-structural zeolite whose crystals are grouped in aggregates that have a grain size with a value of Dv,90 less than or equal to 360 microns and at least one metal of group VIII of the periodic table.

27. A process according to claim 1, wherein the crystals grouped in aggregates have a grain size with a value of Dv,90 less than or equal to 200 microns.

28. A process according to claim 1, wherein the crystals grouped in aggregates have a grain size with a value of Dv,90 less than or equal to 50 microns.

* * * * *